(12) United States Patent
Af Ursin et al.

(10) Patent No.: US 6,491,951 B1
(45) Date of Patent: Dec. 10, 2002

(54) SOLUBLE COMPOSITIONS OF TOREMIFENE

(75) Inventors: Kaija Af Ursin, Turku (FI); Jukka Salmia, Kuusisto (FI); Heikki Niskanen, Turku (FI); Pirjo Kortesuo, Parainen (FI); Mikko Kananen, Kuopio (FI); Juha Kiesvaara, Littoinen (FI); Leena Otsomaa, Espoo (FI)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 09/868,180

(22) PCT Filed: Dec. 16, 1999

(86) PCT No.: PCT/FI99/01047

§ 371 (c)(1),
(2), (4) Date: Sep. 4, 2001

(87) PCT Pub. No.: WO00/35486

PCT Pub. Date: Jun. 22, 2000

(30) Foreign Application Priority Data

Dec. 17, 1998 (FI) .................................................. 982734

(51) Int. Cl.[7] .......................... A61K 9/58; A61K 31/56; A61K 31/33; A01N 25/00
(52) U.S. Cl. ...................... 424/487; 514/182; 514/183; 514/785; 604/22; 424/450
(58) Field of Search .................................. 424/426, 450; 514/182, 183, 785; 604/22

(56) References Cited

U.S. PATENT DOCUMENTS

| | | | |
|---|---|---|---|
| 4,696,949 A | 9/1987 | Toivola et al. ............... | 514/648 |
| 5,571,534 A | 11/1996 | Jalonen et al. ............... | 424/479 |
| 5,859,003 A | 1/1999 | Hettche et al. ........ | 514/217.05 |
| 5,904,930 A | 5/1999 | Fischer et al. .............. | 424/448 |

FOREIGN PATENT DOCUMENTS

| | | |
|---|---|---|
| DE | 293 263 | 8/1991 |
| EP | 0 240 131 | 10/1987 |
| EP | 0 839 533 | 5/1998 |
| EP | 0 842 659 | 5/1998 |
| EP | 0839533 A1 * | 6/1998 |
| EP | 0 893 121 | 1/1999 |
| WO | WO 92/04310 | 3/1992 |
| WO | WO 93/19746 | * 10/1993 |
| WO | WO 94/16733 | 8/1994 |
| WO | WO 97/45367 | 12/1997 |

OTHER PUBLICATIONS

Derwent Abstract of DD 293 263.

* cited by examiner

Primary Examiner—José G. Dees
Assistant Examiner—Robert M DeWitty
(74) Attorney, Agent, or Firm—Finnegan, Henderson, Farabow, Garrett & Dunner, L.L.P.

(57) ABSTRACT

Aqueous compositions of toremifene or a pharmaceutically acceptable salt thereof, comprising lactic acid, acetic acid, formic acid, methanesulfonic acid or the corresponding anion (lactate, acetate, formate or mesylate) as a solubility enhancing agent. Novel salts of toremifene with an acid selected from the group consisting of lactic acid, acetic acid, formic acid or methanesulfonic acid.

13 Claims, No Drawings

SOLUBLE COMPOSITIONS OF TOREMIFENE

This application is a national stage filing of PCT International Application No. PCT/F199/01047, filed on Dec. 16, 1999, which published in the English language. This application also claims the benefit of priority under 35 U.S.C. §119(a) to Finnish patent application no. 982734, filed on Dec. 17, 1998.

BACKGROUND OF THE INVENTION

The present invention relates to aqueous solutions of toremifene or a pharmaceutically acceptable salt thereof for pharmaceutical use and to methods for the preparation thereof. The invention also relates to novel salts of toremifene useful in the preparation of water-soluble formulations, in particular aqueous solutions, of toremifene.

Toremifene is a triphenylethylene antiestrogen useful in the treatment of cancer. The preparation of toremifene and its salts is described in U.S. Pat. No. 4,696,949. The salts described are citric and hydrochloride salts. Toremifene is commercially used as a citrate salt. Toremifene base as well as its citrate and hydrochloride salts are poorly soluble in water. Therefore there is a need for stable aqueous formulations of toremifene which would be suitable for e.g. high concentration parenteral, transdermal or topical formulations of toremifene. Parenteral formulations of toremifene in the form of an emulsion, liposome or cyclodextrin complex have been described in WO 93/11757. Transdermal formulations of toremifene in DMSO/ethanol/methylcellulose/water have been described in WO 93/19746. However, these prior formulations are cumbersome to prepare, are irritating or do not provide sufficiently high concentration solutions of toremifene.

SUMMARY OF THE INVENTION

It has been found that aqueous solutions of toremifene with high drug concentrations can be prepared by using lactic acid, acetic acid, formic acid, methanesulfonic acid or the corresponding anion (lactate, acetate, formate or mesylate) as a solubility enhancing agent. Furthermore, it was found that toremifene forms stable salts with these anions, and these novel salts are useful in the preparation of water-soluble formulations, in particular aqueous solutions, of toremifene.

DETAILED DESCRIPTION OF THE INVENTION

The present invention provides an aqueous composition of toremifene or a pharmaceutically acceptable salt thereof comprising lactic acid, acetic acid, formic acid, methanesulfonic acid or the corresponding anion (lactate, acetate, formate or mesylate) as a solubility enhancing agent.

The present invention also provides a method for preparing aqueous composition of toremifene or a pharmaceutically acceptable salt thereof comprising contacting toremifene or a pharmaceutically acceptable salt thereof with aqueous media and a solubility enhancing agent selected from the group consisting of lactic acid, acetic acid, formic acid, methanesulfonic acid or the corresponding anion (lactate, acetate, formate or mesylate).

Furthermore, the present invention provides a novel salt of toremifene with an acid selected from the group consisting of lactic acid, acetic acid, formic acid or methanesulfonic acid. The novel salts are toremifene lactate, toremifene acetate, toremifene formate and toremifene mesylate.

The compositions of the invention can be prepared e.g. by mixing an amount of a solubility enhancing acid of the invention and purified water, adding thereafter toremifene base or a pharmaceutically acceptable salt thereof and agitating the mixture. pH may be adjusted with a water solution of corresponding acid salt or e.g. sodium hydroxide. The solubility enhancing agent is preferably used in molar excess with respect to toremifene or a pharmaceutically acceptable salt thereof. More preferably, the molar excess is at least about 1.5 fold, and most preferably at least about 2 fold, e.g. from about 2 to about 100 fold, typically from about 2 to about 10 fold.

For example, up to about 50 w-% solutions of toremifene base can be prepared by adding a two fold molar excess of lactic acid and purified water. When pH is adjusted to about 5 with sodium hydroxide, still about 36 w-% solutions of toremifene base can be prepared. Generally, when pH is increased, solubility is decreased. The optimum pH range for the solution is about 6 or lower, due to the pKa value (8.0) of toremifene. Various additives used in the art such as preservatives, e.g. parabens, sodium benzoate or benzoic acid, or various combinations thereof may be used.

The salts of toremifene with lactic acid, acetic acid, formic acid or methanesulfonic acid can be prepared by dissolving toremifene base in suitable organic solvent together with an equivalent amount of lactic acid, acetic acid, formic acid or methanesulfonic acid. The mixture is refluxed and cooled. The formed salt is recovered by filtering or by evaporating to dryness. Suitable organic solvents include lower alcohols and ethers, preferably methanol or diethyl ether. The salts can be formulated into any one of a number of known dosage forms or delivery systems by means known in the art e.g. for oral, parenteral, transdermal or topical use. Preferably the salts of the invention are used for preparing aqueous formulations of toremifene. The salts of the invention have generally improved water solubility over toremifene citrate. For example, the solubility of toremifene mesylate in distilled water is about 70 times higher.

The following experiments demonstrate that the water-solubility of toremifene base can be dramatically improved by using a solubility enhancing agent of the invention. The experiments also compare the effect of solubility enhancing agents of the invention to other acids such as hydrochloric acid, gluconic acid or citric acid.

EXPERIMENTS

EXAMPLE 1

Aqueous formulation of toremifene base using acetic acid as a solubility enhancing agent (% is calculated by weight of the composition)

| | |
|---|---|
| Toremifene base | 18.4% |
| Glacial acetic acid | 9.0% |
| Purified water | 72.6% |

Glacial acetic acid and purified water were mixed, toremifene base was added and dissolved. pH of the solution was about 4.

EXAMPLE 2

Aqueous formulation of toremifene base using lactic acid as a solubility enhancing agent

|  |  |
| --- | --- |
| Toremifene base | 52.6% |
| Lactic acid (85%) | 24.0% |
| Purified water | 23.4% |

Lactic acid (85% water solution) and purified water were mixed, toremifene base was added and dissolved.

EXAMPLE 3

Aqueous formulation of toremifene base using formic acid as a solubility enhancing agent

|  |  |
| --- | --- |
| Toremifene base | 8.2% |
| Formic acid | 1.6% |
| Purified water | 90.2% |

Formic acid and purified water were mixed, toremifene base was added and dissolved.

EXAMPLE 4

Aqueous formulation of toremifene base using methanesulfonic acid as a solubility enhancing agent

|  |  |
| --- | --- |
| Toremifene base | 16.7% |
| Methanesulfonic acid | 66.6% |
| Purified water | 16.7% |

Toremifene base was dissolved in methanesulfonic acid, then purified water was added. A clear solution was obtained.

EXAMPLE 5

Aqueous formulation of toremifene base using lactic acid/lactate as a solubility enhancing agent, pH 5

|  |  |
| --- | --- |
| Toremifene base | 3.7% |
| Lactic acid (85%) | 1.7% |
| Sodium lactate (50%) | 4.4% |
| Purified water | 90.2% |

Lactic acid (85% water solution) and purified water were mixed, toremifene base was added and dissolved. pH was adjusted to about 5 by sodium lactate (50% water solution).

EXAMPLE 6

Aqueous formulation of toremifene base using lactic acid as a solubility enhancing agent, pH 5

|  |  |
| --- | --- |
| Toremifene base | 36.3% |
| Lactic acid (85%) | 18.2% |
| Sodium hydroxide 2 N | 27.3% |
| Purified water | 18.2% |

Manufactured as above but pH was adjusted to about 5 with sodium hydroxide.

EXAMPLE 7
(Reference)

|  |  |
| --- | --- |
| Toremifene base | 9.1% |
| Hydrochlorid acid 1 N | 31.8% |
| Purified water | 59.1% |

Hydrochloric acid and purified water were mixed, toremifene base was added. Toremifene was not dissolved.

EXAMPLE 8
(Reference)

|  |  |
| --- | --- |
| Toremifene base | 1.0% |
| Sodium gluconate | 1.0% |
| Concentrated hydrochlorid acid | 1.0% |
| Purified water | 97.0% |

Sodium gluconate, concentrated hydrochloric acid and purified water were mixed, toremifene base was added. Toremifene was not dissolved.

EXAMPLE 9
(Reference)

|  |  |
| --- | --- |
| Toremifene base | 1.0% |
| Citric acid (30%) | 10.3% |
| Ethanol | 88.7% |

Toremifene base and 30% water solution of citric acid were mixed together and ethanol was added gradually. Toremifene was not dissolved.
Synthesis of Novel Salts of Toremifene
Toremifene Mesylate To a solution of toremifene base (1.094 g, 0.0027 moles) and refluxing diethyl ether (15 ml) was slowly added methanesulfonic acid (190 µl, 0.0029 moles). The refluxing mixture was stirred for a while and cooled to room temperature. The mixture was stirred additional 30 min. After filtration the mesylate of toremifene was obtained (yield 95%) having melting point of 185° C. $^1$H-NMR (d$_6$-DMSO) d 7.41 (t, 2H), 7.35–7.27 (m, 3H), 7.27–7.12 (m, 5H), 6.81 (d, 2H), 6.69 (d, 2H), 4.18 (t, 2H), 3.43 (t, 4H), 2.85 (t, 2H), 2.82 (s, 6H), 2.32 (s, 3H).

Toremifene Formate

To a solution of toremifene base (1.00 g, 0.0025 moles) and refluxing diethyl ether (14 ml) was slowly added formic acid (100 µl, 0.0027 moles). The refluxing mixture was stirred for a while and cooled to room temperature. The mixture was stirred additional 30 min at room temperature. The salt was crystallised at −15° C. for 36 hours. After filtration the formate of toremifene was obtained (yield 78%) having melting point of 147° C. $^1$H-NMR (d$_6$-DMSO) d 8.19 (s, 1H), 7.39 (t, 2H), 7.35–7.27 (m, 3H), 7.27–7.12 (m, 5H), 6.76 (d, 2H), 6.62 (d, 2H), 3.95 (t, 2H), 3.43 (t, 2H 2.85 (t, 2H), 2.70 (t, 2H), 2.28 (s, 6H).

Toremifene Acetate

To a solution of toremifene base (1.00 g, 0.0025 moles) and methanol (20 ml) was slowly added acetic acid (160 µl, 0.0028 moles). The mixture was stirred for a while and evaporated to dryness. The acetate of toremifene was obtained as sticky white solid. $^1$H-NMR (d$_4$-MeOH) d 7.37

(tt, 2H), 7.33–7.25 (m, 3H), 7.25–7.10 (m, 5H), 6.82 (dt, 2H), 6.63 (dt, 2H), 4.08 (t, 2H), 3.39 (t, 2H), 3.09 (t, 2H), 2.89 (t, 2H), 2.60 (s, 6H), 1.92 (s, 3H).

Toremifene Lactate

To a solution of toremifene base (1.00 g, 0.0025 moles) and methanol (20 ml) was slowly added lactic acid (223 μl, 0.0025 moles). The mixture was stirred for a while and evaporated to dryness. The lactate of toremifene was obtained as sticky white solid. $^1$H-NMR ($d_6$-DMSO) d 7.38 (tt, 2H), 7.35–7.27 (m, 3H), 7.27–7.12 (m, 5H), 6.76 (d, 2H), 6.61 (d, 2H), 3.99 (q, 1H), 3.92 (t, 2H), 3.43 (t, 2H), 2.85 (t, 2H), 2.62 (t, 2H), 2.22 (s, 6H), 1.22 (d, 3H).

What is claimed is:

1. An aqueous solution of toremifene or a pharmaceutically acceptable salt thereof, comprising the toremifene or pharmaceutically acceptable salt thereof and lactic acid, acetic acid, formic acid, methanesulfonic acid or the corresponding lactate, acetate, formate or mesylate anion thereof as a solubility enhancing agent.

2. An aqueous solution of claim 1, having a pH value of about 6 or lower.

3. An aqueous solution of claim 1, wherein the solubility enhancing agent is used in molar excess with respect to toremifene or the pharmaceutically acceptable salt thereof.

4. An aqueous solution of claim 3, wherein the molar excess is at least about 1.5 fold.

5. An aqueous solution of claim 4, wherein the molar excess is from about 2 to about 10 fold.

6. A method for preparing an aqueous solution of toremifene or a pharmaceutically acceptable salt thereof, comprising contacting toremifene or the pharmaceutically acceptable salt thereof with aqueous media and a solubility enhancing agent selected from the group consisting of lactic acid, acetic acid, formic acid and methanesulfonic acid or the corresponding lactate, acetate, formate or mesylate anion thereof.

7. A salt of toremifene with an acid selected from the group consisting of lactic acid, acetic acid, formic acid or methanesulfonic acid.

8. A salt of claim 7, which is toremifene lactate.

9. A salt of claim 7, which is toremifene acetate.

10. A salt of claim 7, which is toremifene formate.

11. A salt of claim 7, which is toremifene mesylate.

12. An aqueous solution of claim 2, wherein the solubility enhancing agent is used in molar excess with respect to toremifene or the pharmaceutically acceptable salt thereof.

13. An aqueous solution of claim 3, wherein the molar excess is at least about 2 fold.

* * * * *